United States Patent
Al-Mustafa et al.

(10) Patent No.: US 12,352,164 B2
(45) Date of Patent: Jul. 8, 2025

(54) METHOD FOR DOWNHOLE RESERVOIR SAMPLING INLET SELECTION

(71) Applicant: Saudi Arabian Oil Company, Dhahran (SA)

(72) Inventors: Lool Abdulaziz Al-Mustafa, Dhahran (SA); Mohammed Fuad Al-Zayer, Al Qatif (SA); Faisal Naif Al-Enezi, Dammam (SA)

(73) Assignee: Saudi Arabian Oil Company, Dhahran (SA)

(*) Notice: Subject to any disclaimer, the term of this patent is extended or adjusted under 35 U.S.C. 154(b) by 352 days.

(21) Appl. No.: 17/898,131

(22) Filed: Aug. 29, 2022

(65) Prior Publication Data

US 2024/0068365 A1    Feb. 29, 2024

(51) Int. Cl.
*E21B 49/10* (2006.01)
*G01N 33/28* (2006.01)
*G01V 11/00* (2006.01)

(52) U.S. Cl.
CPC ......... *E21B 49/10* (2013.01); *G01N 33/2823* (2013.01); *G01V 11/002* (2013.01)

(58) Field of Classification Search
CPC ..... G01N 33/2823; E21B 49/08; E21B 49/10; E21B 2200/20; G01V 11/002
USPC ............................................. 702/12
See application file for complete search history.

(56) References Cited

U.S. PATENT DOCUMENTS

| 7,650,937 | B2 | 1/2010 | Fox et al. |
| 8,245,781 | B2 | 8/2012 | Ciglenec et al. |
| 11,371,345 | B2 * | 6/2022 | Olapade ................ E21B 49/08 |
| 2009/0211752 | A1 | 8/2009 | Goodwin et al. |
| 2014/0208826 | A1 | 7/2014 | Larter et al. |
| 2023/0054254 | A1 * | 2/2023 | Jones .................... G01N 33/24 |

OTHER PUBLICATIONS wikipedia.com [online], "Slickline," available on or before Apr. 2010, retrieved Nov. 13, 2022, retrieved from URL <https://en.wikipedia.org/wiki/Slickline#:~:text=Slickline%20refers%20to%20a%20single>, 7 pages.

* cited by examiner

*Primary Examiner* — John H Le
(74) *Attorney, Agent, or Firm* — Fish & Richardson P.C.

(57) ABSTRACT

The present disclosure provides method for managing a set of downhole sampling tools each comprising a respective inlet probe, the method comprising: accessing a database hosting records of operating the set of downhole sampling tools when sampling reservoir formations; identifying a parameter that characterizes a duration from a first time point when one of the set of downhole sampling tool is activated to a second time point when the respective inlet probe on the downhole sampling tool detects a reservoir fluid from the reservoir formations; measuring, using the identified parameter, performances of the set of downhole sampling tools; and at least based on the measured performances, selecting, from the set of downhole sampling tools, a particular downhole sampling tool such that the particular downhole sampling tool is deployed for at least one upcoming downhole sampling job.

20 Claims, 7 Drawing Sheets

METHOD FOR DOWNHOLE RESERVOIR SAMPLING INLET SELECTION

TECHNICAL FIELD

This disclosure generally relates to downhole sampling during oil and gas exploration.

BACKGROUND

During oil and gas exploration, downhole sample is often used to test reservoir formations. Formation testers can use a class of wireline tools to measure, for example, downhole pressure of formations. In some cases, stationary measurements of formation pressure in an open hole are made at a number of depths during a single trip into the hole. In general, the downhole formation sampling process can be a risky and costly dynamic operation.

SUMMARY

In one aspect, the present disclosure describes a computer-assisted method for managing a set of downhole sampling tools each comprising a respective inlet probe, the method including: accessing a database hosting records of operating the set of downhole sampling tools when sampling reservoir formations; identifying a parameter that characterizes a duration from a first time point when one of the set of downhole sampling tool is activated to a second time point when the respective inlet probe on the downhole sampling tool detects a reservoir fluid from the reservoir formations; measuring, using the identified parameter, performances of the set of downhole sampling tools; and at least based on the measured performances, selecting, from the set of downhole sampling tools, a particular downhole sampling tool such that the particular downhole sampling tool is deployed for at least one upcoming downhole sampling job.

Implementations may include one or more of the following features.

The method may further include: selecting the particular downhole sampling tool whose respective performance measured using the identified parameter is better than those of other downhole sampling tools from the set of downhole sampling tools. Selecting the particular downhole sampling tool may further include: filtering the records of operating the set of downhole sampling tools based on at least one of: a formation type or a formation mobility with respect to the reservoir formations being sampled.

The method may further include: providing, to the database, records of conducting at least one upcoming downhole sampling job using the particular downhole sampling tool. The method may further include: measuring, based on updated records of operating the set of downhole sampling tools, performances of the set of downhole sampling tools. The method may further include: in response to the measured performances indicating the respective performance of the particular downhole sampling tool has deteriorated, selecting, from the set of downhole sampling tools, another downhole sampling tool. Each respective inlet probe may include one of: a fluid sound speed sensor, a fluid density sensor, a fluid capacitance sensor, a fluid resistivity sensor, a gas refractometer, or an optical absorption spectrometry.

In another aspect, implementations of the present disclosure describes a computer system for managing a set of downhole sampling tools each comprising a respective inlet probe, the computer system comprising one or more computer processors configured to perform operations of: accessing a database hosting records of operating the set of downhole sampling tools when sampling reservoir formations; identifying a parameter that characterizes a duration from a first time point when one of the set of downhole sampling tool is activated to a second time point when the respective inlet probe on the downhole sampling tool detects a reservoir fluid from the reservoir formations; measuring, using the identified parameter, performances of the set of downhole sampling tools; and at least based on the measured performances, selecting, from the set of downhole sampling tools, a particular downhole sampling tool such that the particular downhole sampling tool is deployed for at least one upcoming downhole sampling job.

Implementations may include one or more of the following features.

The operations may further include: selecting the particular downhole sampling tool whose respective performance measured using the identified parameter is better than those of other downhole sampling tools from the set of downhole sampling tools. Selecting the particular downhole sampling tool may further include: filtering the records of operating the set of downhole sampling tools based on at least one of: a formation type or a formation mobility with respect to the reservoir formations being sampled.

The operations may further include: providing, to the database, records of conducting at least one upcoming downhole sampling job using the particular downhole sampling tool. The operations may further include: measuring, based on updated records of operating the set of downhole sampling tools, performances of the set of downhole sampling tools. The operations may further include: in response to the measured performances indicating the respective performance of the particular downhole sampling tool has deteriorated, selecting, from the set of downhole sampling tools, another downhole sampling tool. Each respective inlet probe may include one of: a fluid sound speed sensor, a fluid density sensor, a fluid capacitance sensor, a fluid resistivity sensor, a gas refractometer, or an optical absorption spectrometry.

In yet another aspect, implementations of the present disclosure describes a non-transitory computer-readable medium comprising software instructions, which, when executed by one or more computer processors, cause the one or more computer processors to perform operations of: accessing a database hosting records of operating the set of downhole sampling tools when sampling reservoir formations; identifying a parameter that characterizes a duration from a first time point when one of the set of downhole sampling tool is activated to a second time point when the respective inlet probe on the downhole sampling tool detects a reservoir fluid from the reservoir formations; measuring, using the identified parameter, performances of the set of downhole sampling tools; and at least based on the measured performances, selecting, from the set of downhole sampling tools, a particular downhole sampling tool such that the particular downhole sampling tool is deployed for at least one upcoming downhole sampling job.

Implementations may include one or more of the following features.

The operations may further include: selecting the particular downhole sampling tool whose respective performance measured using the identified parameter is better than those of other downhole sampling tools from the set of downhole sampling tools. Selecting the particular downhole sampling tool may further include: filtering the records of operating the set of downhole sampling tools based on at least one of:

a formation type or a formation mobility with respect to the reservoir formations being sampled.

The operations may further include: providing, to the database, records of conducting at least one upcoming downhole sampling job using the particular downhole sampling tool. The operations may further include: measuring, based on updated records of operating the set of downhole sampling tools, performances of the set of downhole sampling tools. The operations may further include: in response to the measured performances indicating the respective performance of the particular downhole sampling tool has deteriorated, selecting, from the set of downhole sampling tools, another downhole sampling tool. Each respective inlet probe may include one of: a fluid sound speed sensor, a fluid density sensor, a fluid capacitance sensor, a fluid resistivity sensor, a gas refractometer, or an optical absorption spectrometry.

Implementations according to the present disclosure may be realized in computer implemented methods, hardware computing systems, and tangible computer readable media. For example, a system of one or more computers can be configured to perform particular actions by virtue of having software, firmware, hardware, or a combination of them installed on the system that in operation causes or cause the system to perform the actions. One or more computer programs can be configured to perform particular actions by virtue of including instructions that, when executed by data processing apparatus, cause the apparatus to perform the actions.

The details of one or more implementations of the subject matter of this specification are set forth in the description, the claims, and the accompanying drawings. Other features, aspects, and advantages of the subject matter will become apparent from the description, the claims, and the accompanying drawings.

DESCRIPTION OF DRAWINGS

Like reference numbers and designations in the various drawings indicate like elements.

DETAILED DESCRIPTION

The disclosed technology is directed to systems and methods for judicious operation of wireline downhole sampling for reservoir formations. Some implementations start with identifying a set of parameters that impact the accuracy and efficiency of downhole wireline sampling more agilely than other parameters. One example of such parameter is the temporal duration for the probe of a downhole sampling configuration to first identify reservoir fluid. Thereafter, the implementations can obtain performance of various configurations of downhole wirelines (e.g., sampling inlets) as measured based on the identified set of parameters. The implementation may then select the configuration whose performance is better than those of other configurations, leading to, for example, a particular inlet probe for sampling/testing. The implementations may then deploy the particular inlet probe for sampling/testing on-site. The technology can utilize vast information from a large database hosting information of downhole formation sampling properties that cover a wide range of tools and configurations. Once the optimized inlet probe is deployed, the implementations may continue monitoring the performance of the downhole sampling configurations that use, for example, the particular inlet probe.

Oil and gas explorations often create wellbores at drilling sites. Using a wireline (sometimes known as a slick line), operations often launch a downhole sampling tool, which can mount, for example, a variety of inlet probes to sample reservoir formations at various depths. A wireline refers to, for example, a single strand wire which is used to run a variety of tools down into the wellbore for several purposes. A wireline is often used during well drilling operations in the oil and gas industry. In this context, downhole formation sampling is generally risky and costly dynamic operation. Some implementations of the present disclosure aims at reducing the risk, the time, and the cost associated with obtaining downhole reservoir sample when performance of the downhole sampling configurations varies between service providers and the sampling inlet type being used by each service provider.

Figure 1:
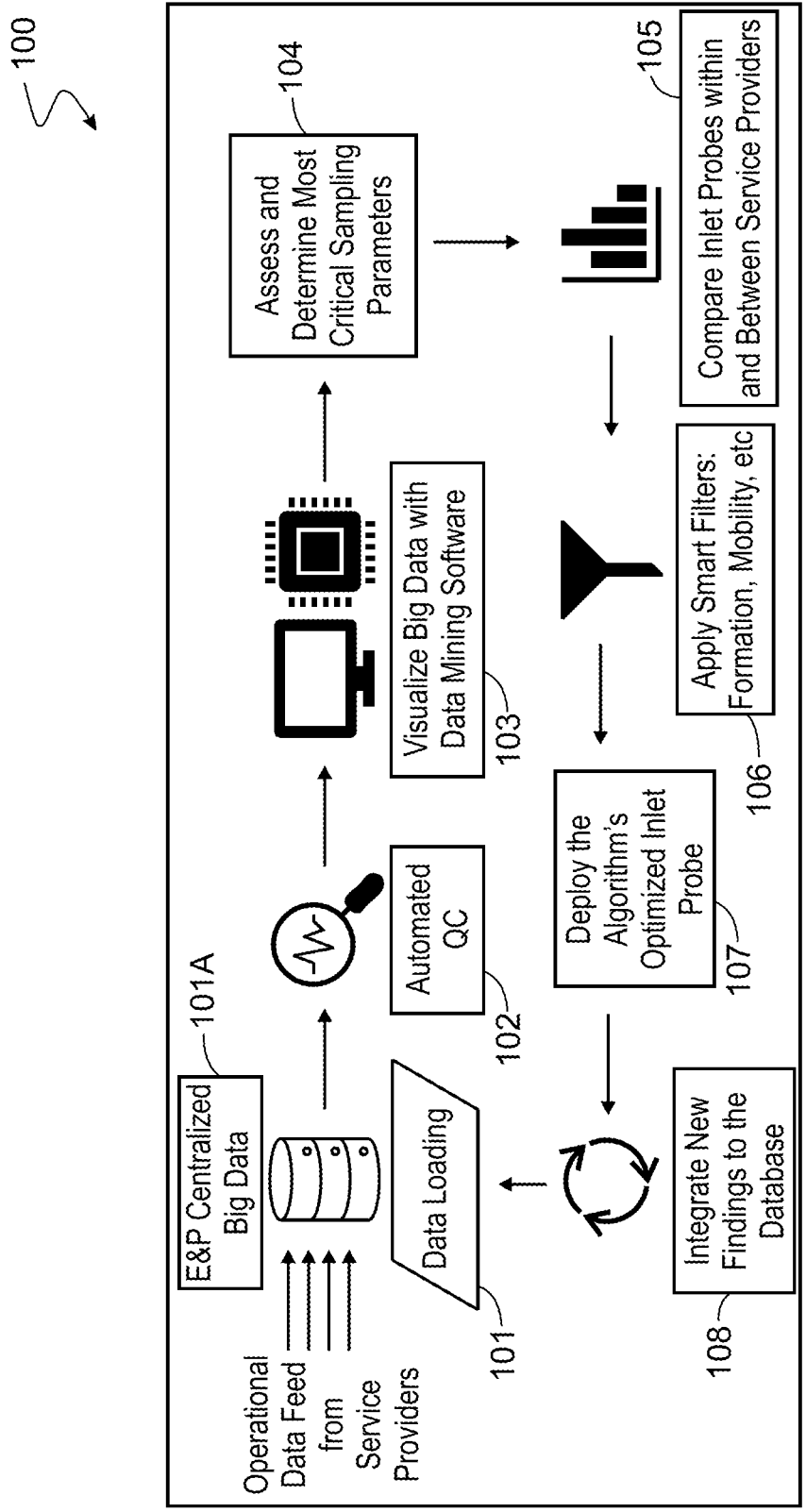
FIG. 1 illustrate an example of a method to iteratively optimize downhole reservoir sampling inlet selection (SIS) according to an implementation of the present disclosure.

Referring to FIG. 1, diagram 100 illustrates an example of a process for downhole reservoir sampling inlet selection (SIS) according to some implementations. The process can identify the a preferred downhole formation sampling inlet probe that results in significant cost and operational time savings. The process may leverage the power of big data visualization techniques as well as operational know-how to arrive at a judicious choke of a sampling probe, for example, at a particular location or drilling site. As illustrated, the process revolves around leveraging big data and starts with data loading (101) from, for example, a large database 101A. The database 101A can be coupled to operational data feed from service providers. The operational data feed may be provided in realtime. In some cases, the process may load 10,000+ downhole sampling data points with 89 different characterizing metrics including, for example, temperature, pump rate, contamination percentage. The metrics generally refer to parameters that each characterizes an operational aspect of a downhole sampling configuration. A performance of the downhole sampling configuration can be measured based on a corresponding parameter, for example, temperate, pressure, pump rate, or contamination rate. Because each downhole sampling configurations can incorporate, for example, components such as inlet probe types that vary greatly from one configuration to another configuration.

Figure 2A:
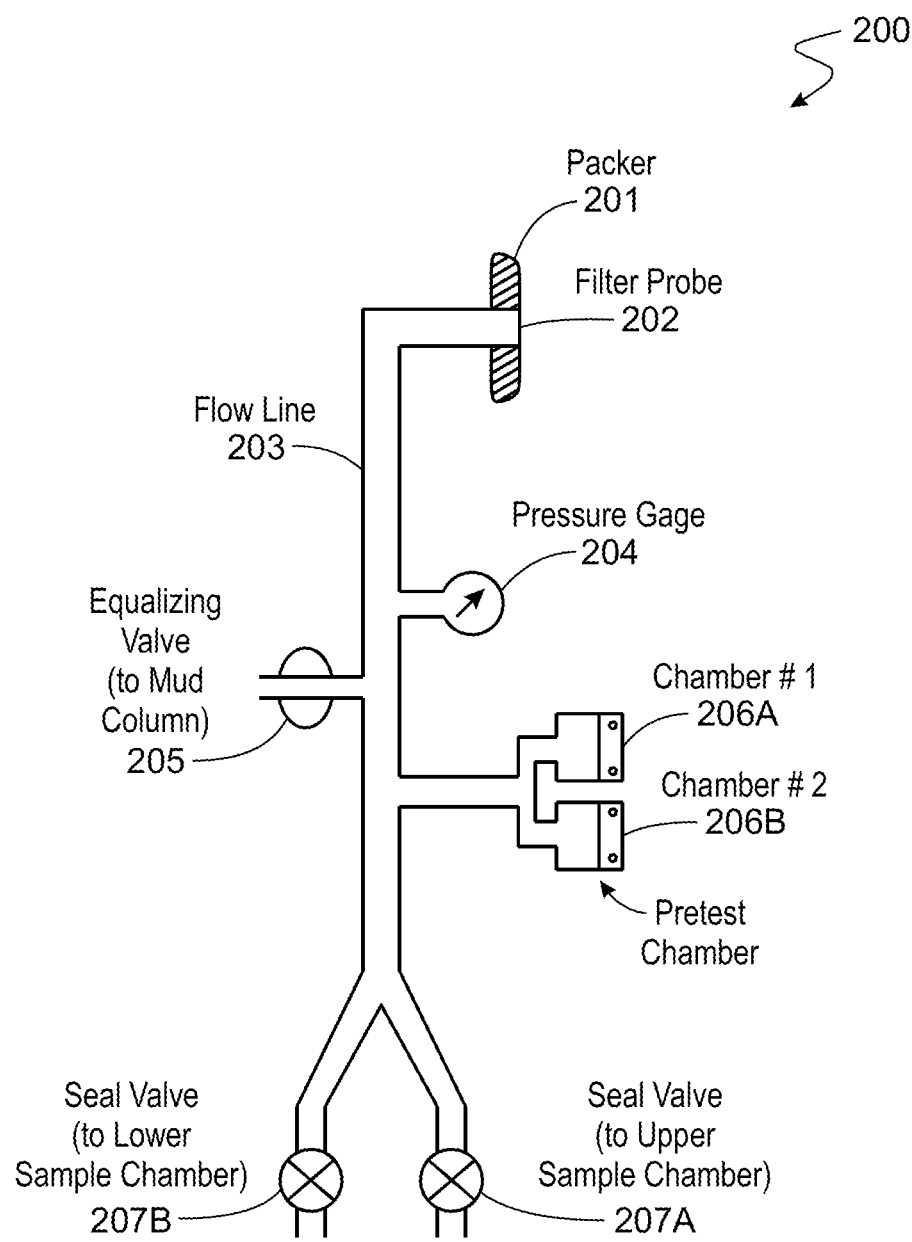
FIGS. 2A to 2E illustrate examples of inlet probe configurations according to some implementations of the present disclosure.

For context, a downhole sampling operation may utilize multiple modular tools including, for example, pumps, pipes, inlet probes, and sensors to identify reservoir fluid at specific depth and then obtain a clean sample for lab testing. Further referring to FIG. 2A, an example of a downhole sampling system 200 includes packer 201, filter probe 202, flow line 203, pressure gage 204, equalizing valve 205, chambers 206A and 206B, seal valves 207A and 207B. Prior to activating system 200, the pressure gauge 204 measures hydrostatic mud column pressure. Upon activation, the equalizing valve 205 is shut and the packer 201 and filter probe 202 are pushed against the formation. The sampling system 200 is now set. Within a few seconds, the pistons of the pretest chambers (including chambers 206A and 206B) begin to withdraw, causing fluid from the formation to flow into the sampling 1 through the packer 201 and probe 202. The pretests can be done sequentially with a small volume (e.g., 10 cc) of fluid drawn into chamber 206A over about 15 sec, followed by a similar volume flowing into chamber 206B at a higher flow rate. Upon completion of the pretests, a sample can be taken or the sampling system 200 can be retracted. During retraction, the equalizing valve 205 may be opened and the pretest pistons at chambers 206A and 206B expel the fluid taken in. The sampling system 200 is now ready for the next test depth.

Figure 2B:
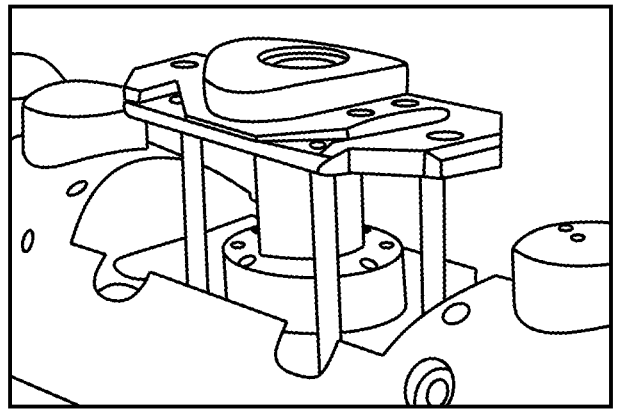
Figure 2C:
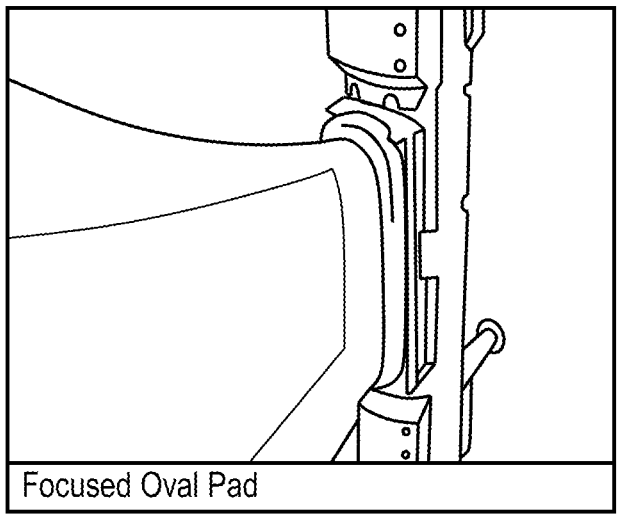
Figure 2D:
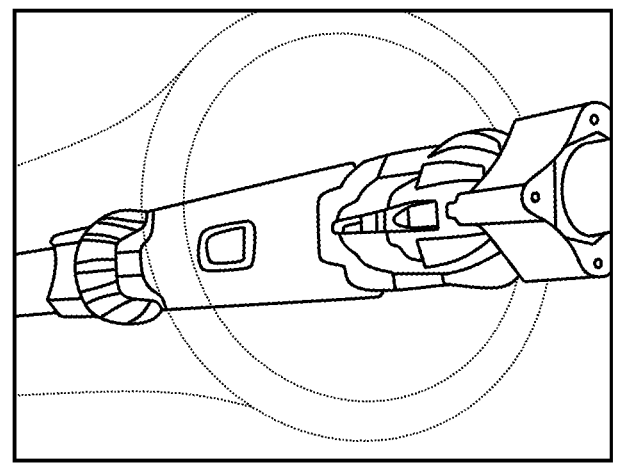
Figure 2E:
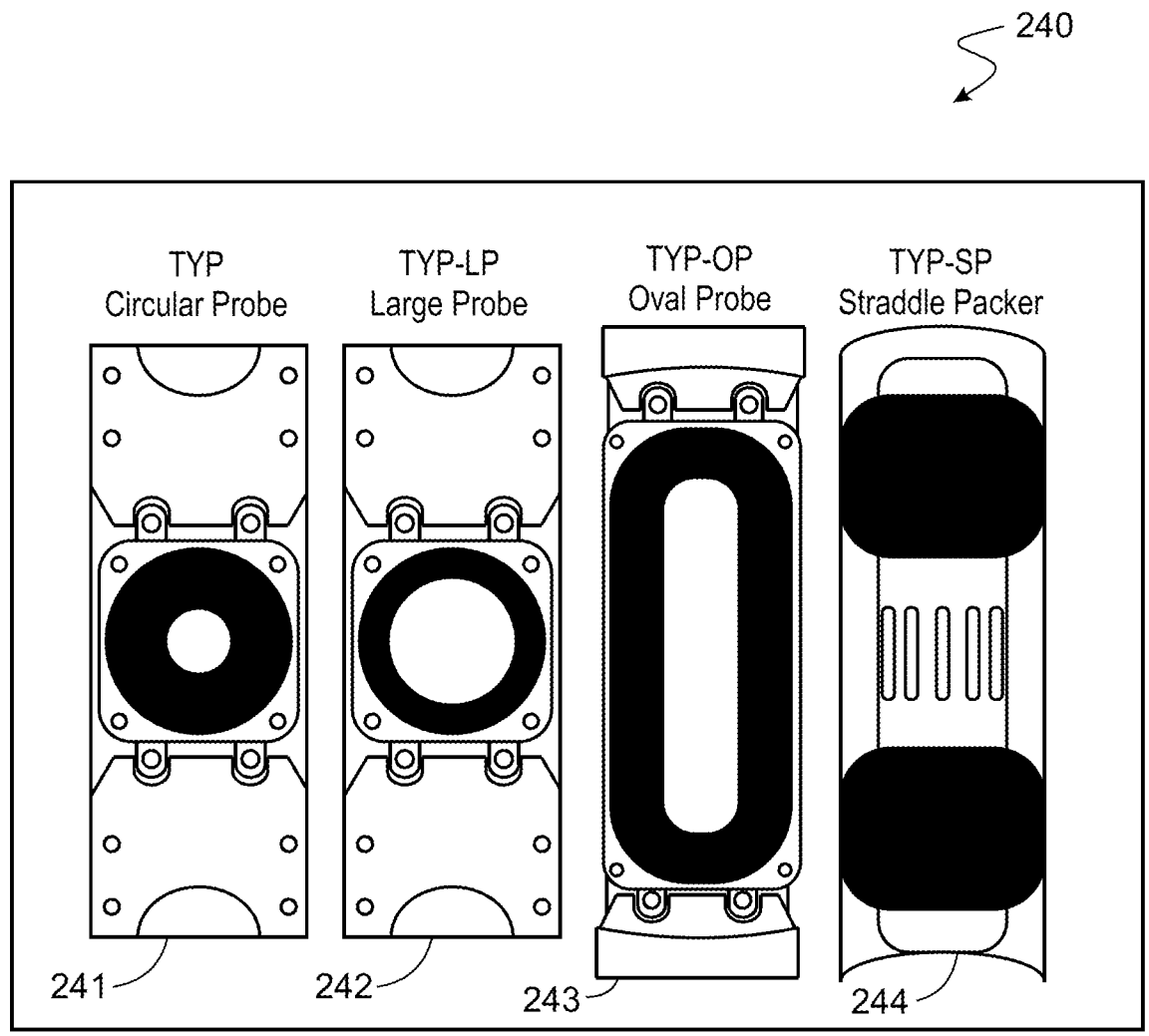

Notably, different vendors may use variations of this sampling system 200 that incorporate a single pretest chamber of fixed or variable volume. Further referring to FIGS. 2B to 2E, the inlet probes (e.g., filter probe 202) may be configured in different types between contractors and service providers. FIG. 2B illustrates an example of a small circular probe 210. FIG. 2C illustrates an example of an elongated probe 220, which operates with two simultaneous pumps, FIG. 2I) illustrates an example of a single rubber element 230, The arrangements can result in unexpected variations in the effectiveness of the sampling operation. Implementations of the present disclosure can provide practical solutions to manage these variations, FIG. 2E summarizes an example of a circular probe 241, an example of a large probe 242, an example of an oval probe 243, and an example of a straddle packer 244. The choice of the inlet probe can vary significantly between different service providers, or even from the same service provider. Even the same type of inlet probe can lead to different performances between companies. Therefore, the type of the inlet probe can have major impact on the performance of a downhole sampling job.

Returning to FIG. 1, the process may then perform automated quality control (102). For example, outliers of data points can be removed. Redundant data points can be consolidated. In other words, automated quality control 102 can remove unusual data points and standardize the remaining data points for data consistency. As noted, the downhole sampling processes can be performed by different service providers and with different inlet probes.

Thereafter, the process may visualize data using a data mining software (103), example, a feature-rich big data visualization software may provide seamlessly visualization of the data points, either as an ensemble or with regards to location and numerical filters. Examples can include the Spotfire software.

Based on examining a multitude of parameters through data visualizations, one or more parameters can be identified (104) based on which a sampling probe configuration can be selected for upcoming downhole sampling jobs. Due to the dynamic nature of downhole formation sampling operations, many parameters of the downhole sampling process can be affected by external factors in addition to a combination of the sampling objective and the subjective judgment of the engineers executing and monitoring the job. Some implementations thus focus on objective parameters that may not be skewed with human input. One such parameter is the time it takes a probe to first identify reservoir fluid.

For additional context, the cost intensive sampling process generally starts by setting the inlet probe of a downhole sampling tool at a target sampling depth and then set off pumping fluid at the target sampling depth. Initially, the fluid is made of drilling mud filtrate, also known as the contaminants. After an initial period of time, the identified reservoir fluid may come out. The process may continue pumping and the percentage of reservoir fluid may be increased while the percentage of drilling mud filtrate (contaminant) is reduced. In general, the process may identify sampling fluid type entering the inlet probe using one of many potential devices predicated on different physical concepts. For example, a downhole sampling tool can include a fluid sound speed sensor, a fluid density sensor, a fluid capacitance sensor, a fluid resistivity sensor, a gas refractometer, or an optical absorption spectrometry, each operating by an independent mechanism. For this reason, benchmarking the downhole sampling tools can be challenging.

Various implementations incorporate an object parameter for benchmarking the available downhole sampling tools. For example, after the start of the sampling process, the time when the pumped-out fluid type sensor indicates that the pumped-out fluid has change from being 100% contaminant to a contaminant with a breakthrough amount of reservoir fluid (often in small amount) is readily available in most independent measurement sensors. Such a parameter can be free from human subjective judgment and based on underlying sensors, even though the sensors can vary.

In comparison, when contamination percentage is treated as an objective parameter, the benchmarking process remain challenging because the fluid type sensors operate by different mechanisms, thus leading to different calculation methodologies. The variation generally renders it difficult to verify measurements, thereby giving rise to miscalculations due to inconsistent input or experience level.

However, the time to identify reservoir fluid can be objectively determined and consistently measured in the same way across a spectrum of downhole sampling tools (even those from different service providers). Notably, the service providers have no hidden incentive to misreport this parameter because misreporting this parameter would not impact job specific or overall long-term economics of these service providers. Furthermore, the service providers are monitored constantly by an operating company to enforce data integrity and consistency.

Figure 3:
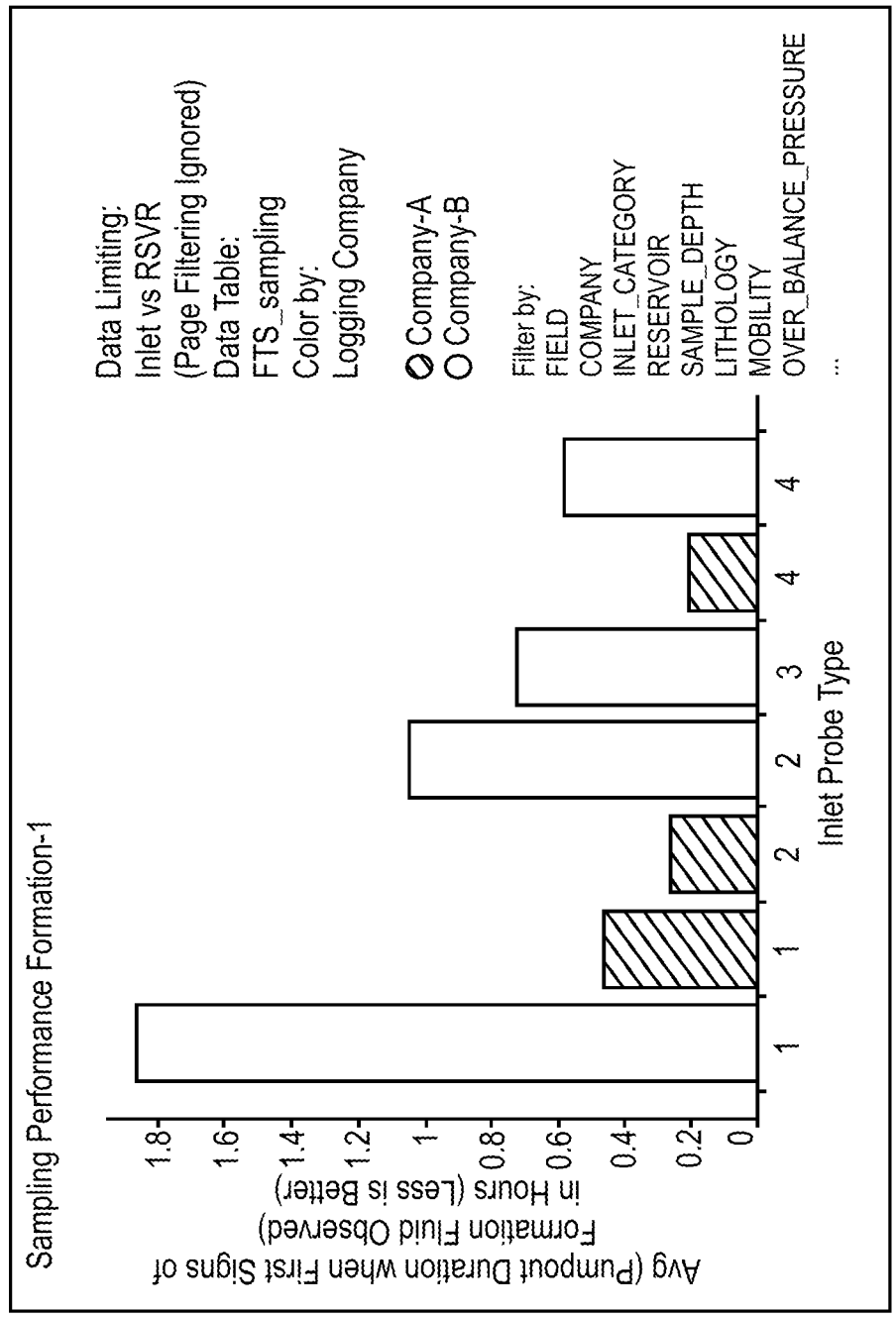
FIG. 3 illustrates an example of results of optimization according to some implementations of the present disclosure.

After identifying the parameter to use, the process may proceed to compare inlet probes used by different downhole sampling tools within and between service providers (105). Further referring to FIG. 3, an example of a comparison is shown. This example shows the performances, as measured by the time for the probe to detect the presence of reservoir fluid, of four (4) inlet probe types from two different service. Here, the measured performance varies. Company-A outperforms Company-B in sampling Formation-1. In addition, within Company-A, inlet Probe Type-4 identified reservoir fluid at an impressive 0.2 hours. Such insight helps identifying the most efficient inlet probe type and can be further filtered to specific rock properties or well location for more specific performance analysis. Indeed, the process, as illustrated in FIG. 1, may proceed to apply smart filters based on, for example, formation type and formation mobility (106). In other words, the implementations may apply additional filtering before selecting one of the many available inlet probes. After an inlet probe is selected, the process may proceed to deploy the inlet probe in a downhole sampling tool for a particular drilling site (107). The downhole sampling tool may generate additional data, which can be integrated into the large database 101A. In other words, new findings can feed into the data loading for continued (and iterative operation).

Figure 4:
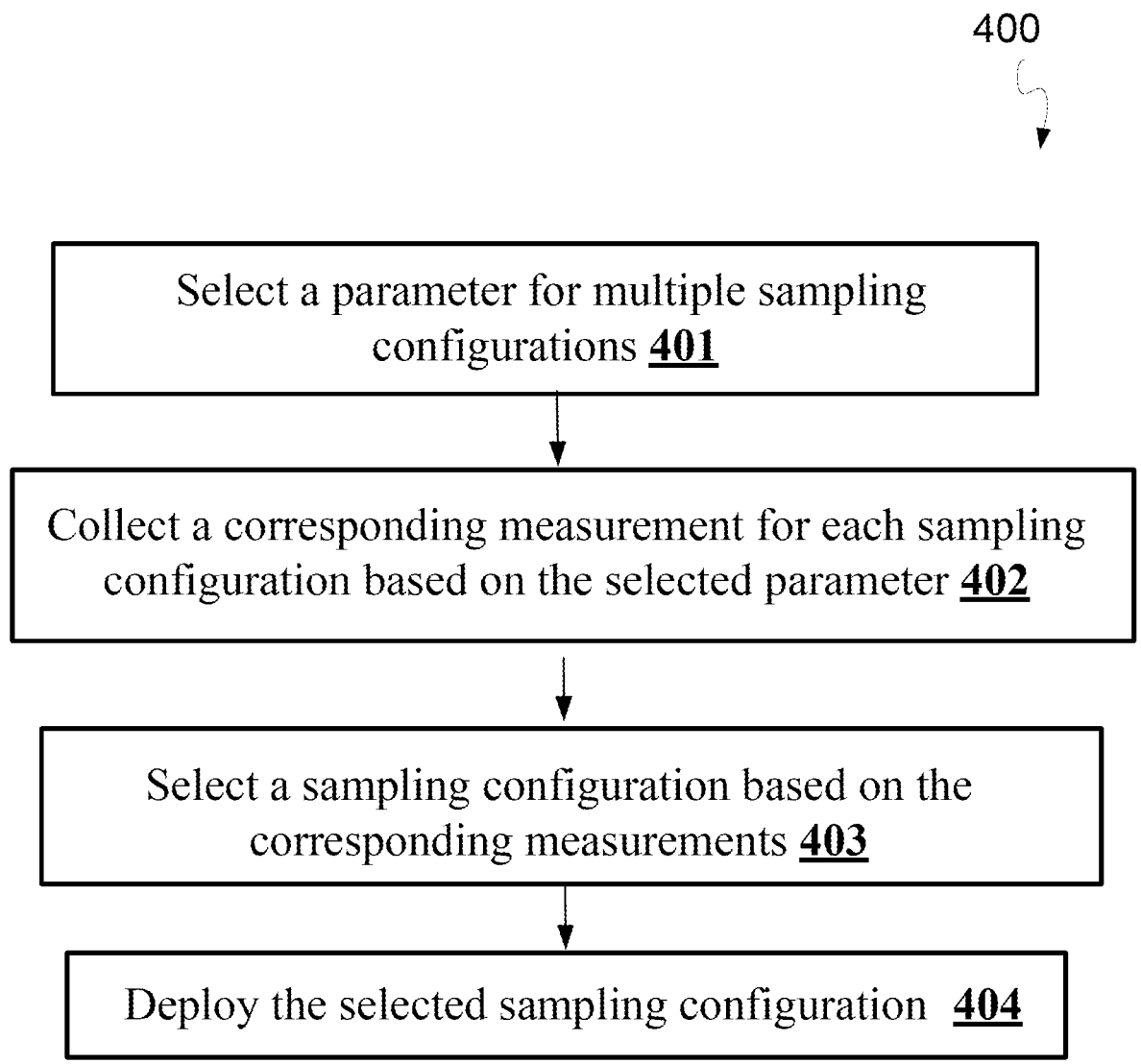
FIG. 4 illustrates an example of a flowchart according to an implementation of the present disclosure.

FIG. 4 is a flowchart 400 showing an example of a process according to some implementations. Initially, an operator may select a parameter for comparing the performances of downhole sampling tools incorporating inlet probes of distinct designs (401). As described above, a downhole sampling tool may be deployed in a wellbore to probe reservoir formation. During this process, a sampling inlet is placed on the target depth, then the fluid pumps can start extracting fluids from the reservoir formation. Initially, the output is filled with contaminants (e.g., filtrate). As the pumping continues, a sample of the reservoir fluid may be captured when the tool sensors indicate low contamination. The duration from the start of pumping to the time when the pumped out fluid changes from being 100% contaminant to a contaminant with a breakthrough of reservoir fluid (often in small amount) can be used as an objective and tool-independent parameter to benchmark the performance of various downhole sampling tools.

The process may then collect performance measurements of the downhole sampling tools measured based on the selected parameter (402). As discussed in association with FIGS. 2A to 2E, the downhole sampling tools can incorporate inlet probes of distinct designs. The choice of the inlet probe can vary significantly between different service providers, or even from the same service provider. Even the same type of inlet probe can lead to different performances between companies. As such, the type of the inlet probe can have major impact on the performance of a downhole sampling job.

Based on the measured performance, the process may then select a downhole sampling tool with a particular inlet probe configuration (403). For example, the process may select the downhole sampling tool with the best performance. In some cases, the process may select the downhole sampling tool that generated the shortest time to detect reservoir fluid. the implementations may apply additional filtering based on, for example, formation type and formation mobility, before selecting one of the many available inlet probes. The selected downhole sampling tool may incorporate a particular inlet probe type.

The process may then deploy the selected downhole sampling tool with the particular inlet probe type for upcoming downhole sampling jobs at a drilling site (404). The downhole sampling tool may then generate additional data of measured performance for the selected downhole sampling tool. In some cases, the process can continue to monitor the influx of the additional data.

Figure 5:
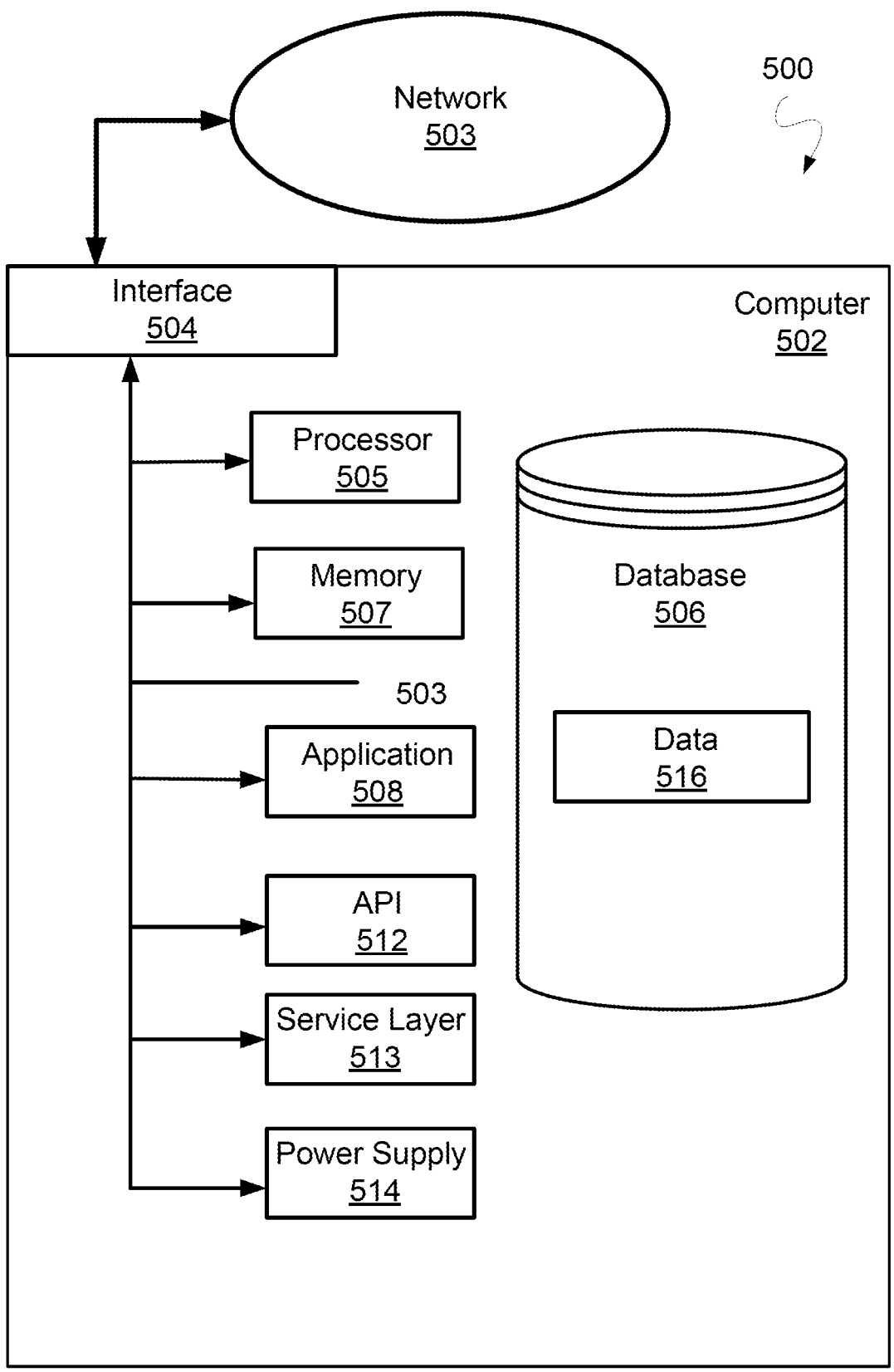
FIG. 5 is a block diagram illustrating an example of a computer system used to provide computational functionalities associated with described algorithms, methods, functions, processes, flows, and procedures, according to an implementation of the present disclosure.

FIG. 5 is a block diagram illustrating an example of a computer system 500 used to provide computational functionalities associated with described algorithms, methods, functions, processes, flows, and procedures, according to an implementation of the present disclosure. The illustrated computer 502 is intended to encompass any computing device such as a server, desktop computer, laptop/notebook computer, wireless data port, smart phone, personal data assistant (PDA), tablet computing device, one or more processors within these devices, another computing device, or a combination of computing devices, including physical or virtual instances of the computing device, or a combination of physical or virtual instances of the computing device. Additionally, the computer 502 can comprise a computer that includes an input device, such as a keypad, keyboard, touch screen, another input device, or a combination of input devices that can accept user information, and an output device that conveys information associated with the operation of the computer 502, including digital data, visual, audio, another type of information, or a combination of types of information, on a graphical-type user interface (UI) (or GUI) or other UI.

The computer 502 can serve in a role in a computer system as a client, network component, a server, a database or another persistency, another role, or a combination of roles for performing the subject matter described in the present disclosure. The illustrated computer 502 is communicably coupled with a network 503. In some implementations, one or more components of the computer 502 can be configured to operate within an environment, including cloud-computing-based, local, global, another environment, or a combination of environments.

The computer 502 is an electronic computing device operable to receive, transmit, process, store, or manage data and information associated with the described subject matter. According to some implementations, the computer 502 can also include or be communicably coupled with a server, including an application server, e-mail server, web server, caching server, streaming data server, another server, or a combination of servers.

The computer 502 can receive requests over network 503 (for example, from a client software application executing on another computer 502) and respond to the received requests by processing the received requests using a software application or a combination of software applications. In addition, requests can also be sent to the computer 502 from internal users, external or third-parties, or other entities, individuals, systems, or computers.

Each of the components of the computer 502 can communicate using a system bus 503. In some implementations, any or all of the components of the computer 502, including hardware, software, or a combination of hardware and software, can interface over the system bus 503 using an application programming interface (API) 512, a service layer 513, or a combination of the API 512 and service layer 513. The API 512 can include specifications for routines, data structures, and object classes. The API 512 can be either computer-language independent or dependent and refer to a complete interface, a single function, or even a set of APIs. The service layer 513 provides software services to the computer 502 or other components (whether illustrated or not) that are communicably coupled to the computer 502. The functionality of the computer 502 can be accessible for all service consumers using this service layer. Software services, such as those provided by the service layer 513, provide reusable, defined functionalities through a defined interface. For example, the interface can be software written in JAVA, C++, another computing language, or a combination of computing languages providing data in extensible markup language (XML) format, another format, or a combination of formats. While illustrated as an integrated component of the computer 502, alternative implementations can illustrate the API 512 or the service layer 513 as stand-alone components in relation to other components of the computer 502 or other components (whether illustrated or not) that are communicably coupled to the computer 502. Moreover, any or all parts of the API 512 or the service layer 513 can be implemented as a child or a sub-module of another software module, enterprise application, or hardware module without departing from the scope of the present disclosure.

The computer 502 includes an interface 504. Although illustrated as a single interface 504 in FIG. 5, two or more interfaces 504 can be used according to particular needs, desires, or particular implementations of the computer 502. The interface 504 is used by the computer 502 for communicating with another computing system (whether illustrated or not) that is communicatively linked to the network 503 in a distributed environment. Generally, the interface 504 is operable to communicate with the network 503 and comprises logic encoded in software, hardware, or a combination of software and hardware. More specifically, the interface 504 can comprise software supporting one or more communication protocols associated with communications such that the network 503 or interface's hardware is operable to communicate physical signals within and outside of the illustrated computer 502.

The computer 502 includes a processor 505. Although illustrated as a single processor 505 in FIG. 5, two or more processors can be used according to particular needs, desires, or particular implementations of the computer 502. Generally, the processor 505 executes instructions and manipulates data to perform the operations of the computer 502 and any algorithms, methods, functions, processes, flows, and procedures as described in the present disclosure.

The computer 502 also includes a database 506 that can hold data for the computer 502, another component communicatively linked to the network 503 (whether illustrated or not), or a combination of the computer 502 and another component. For example, database 506 can be an in-memory, conventional, or another type of database storing data consistent with the present disclosure. In some implementations, database 506 can be a combination of two or more different database types (for example, a hybrid in-memory and conventional database) according to particular needs, desires, or particular implementations of the computer 502 and the described functionality. Although illustrated as a single database 506 in FIG. 5, two or more databases of similar or differing types can be used according to particular needs, desires, or particular implementations of the computer 502 and the described functionality. While database 506 is illustrated as an integral component of the computer 502, in alternative implementations, database 506 can be external to the computer 502. As illustrated, the database 506 holds the previously described data 516 including, for example, operational data from service provides that feed into big data 101A.

The computer 502 also includes a memory 507 that can hold data for the computer 502, another component or components communicatively linked to the network 503 (whether illustrated or not), or a combination of the computer 502 and another component. Memory 507 can store any data consistent with the present disclosure. In some implementations, memory 507 can be a combination of two or more different types of memory (for example, a combination of semiconductor and magnetic storage) according to particular needs, desires, or particular implementations of the computer 502 and the described functionality. Although illustrated as a single memory 507 in FIG. 5, two or more memories 507 or similar or differing types can be used according to particular needs, desires, or particular implementations of the computer 502 and the described functionality. While memory 507 is illustrated as an integral component of the computer 502, in alternative implementations, memory 507 can be external to the computer 502.

The application 508 is an algorithmic software engine providing functionality according to particular needs, desires, or particular implementations of the computer 502, particularly with respect to functionality described in the present disclosure. For example, application 508 can serve as one or more components, modules, or applications. Further, although illustrated as a single application 508, the application 508 can be implemented as multiple applications 508 on the computer 502. In addition, although illustrated as integral to the computer 502, in alternative implementations, the application 508 can be external to the computer 502.

The computer 502 can also include a power supply 514. The power supply 514 can include a rechargeable or non-rechargeable battery that can be configured to be either user- or non-user-replaceable. In some implementations, the power supply 514 can include power-conversion or management circuits (including recharging, standby, or another power management functionality). In some implementations, the power-supply 514 can include a power plug to allow the computer 502 to be plugged into a wall socket or another power source to, for example, power the computer 502 or recharge a rechargeable battery.

There can be any number of computers 502 associated with, or external to, a computer system containing computer 502, each computer 502 communicating over network 503. Further, the term "client," "user," or other appropriate terminology can be used interchangeably, as appropriate, without departing from the scope of the present disclosure. Moreover, the present disclosure contemplates that many users can use one computer 502, or that one user can use multiple computers 502.

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Software implementations of the described subject matter can be implemented as one or more computer programs, that is, one or more modules of computer program instructions encoded on a tangible, non-transitory, computer-readable computer-storage medium for execution by, or to control the operation of, data processing apparatus. Alternatively, or additionally, the program instructions can be encoded in/on an artificially generated propagated signal, for example, a machine-generated electrical, optical, or electromagnetic signal that is generated to encode information for transmission to a receiver apparatus for execution by a data processing apparatus. The computer-storage medium can be a machine-readable storage device, a machine-readable storage substrate, a random or serial access memory device, or a combination of computer-storage mediums. Configuring one or more computers means that the one or more computers have installed hardware, firmware, or software (or combinations of hardware, firmware, and software) so that when the software is executed by the one or more computers, particular computing operations are performed.

The term "real-time," "real time," "realtime," "real (fast) time (RFT)," "near(ly) real-time (NRT)," "quasi real-time," or similar terms (as understood by one of ordinary skill in the art), means that an action and a response are temporally proximate such that an individual perceives the action and the response occurring substantially simultaneously. For example, the time difference for a response to display (or for an initiation of a display) of data following the individual's action to access the data can be less than 1 millisecond (ms), less than 1 second (s), or less than 5 s. While the requested data need not be displayed (or initiated for display) instantaneously, it is displayed (or initiated for display) without any intentional delay, taking into account processing limitations of a described computing system and time required to, for example, gather, accurately measure, analyze, process, store, or transmit the data.

The terms "data processing apparatus," "computer," or "electronic computer device" (or equivalent as understood by one of ordinary skill in the art) refer to data processing hardware and encompass all kinds of apparatus, devices, and machines for processing data, including by way of example, a programmable processor, a computer, or multiple processors or computers. The apparatus can also be, or further include special purpose logic circuitry, for example, a central processing unit (CPU), an FPGA (field programmable gate array), or an ASIC (application-specific integrated circuit). In some implementations, the data processing apparatus or special purpose logic circuitry (or a combination of the data processing apparatus or special purpose logic circuitry) can be hardware- or software-based (or a combination of both hardware- and software-based). The apparatus can optionally include code that creates an execution environment for computer programs, for example, code that constitutes processor firmware, a protocol stack, a database management system, an operating system, or a combination of execution environments. The present disclosure contemplates the use of data processing apparatuses with an operating system of some type, for example LINUX, UNIX, WINDOWS, MAC OS, ANDROID, IOS, another operating system, or a combination of operating systems.

A computer program, which can also be referred to or described as a program, software, a software application, a unit, a module, a software module, a script, code, or other component can be written in any form of programming language, including compiled or interpreted languages, or declarative or procedural languages, and it can be deployed in any form, including, for example, as a stand-alone program, module, component, or subroutine, for use in a computing environment. A computer program can, but need not, correspond to a file in a file system. A program can be stored in a portion of a file that holds other programs or data, for example, one or more scripts stored in a markup language document, in a single file dedicated to the program in question, or in multiple coordinated files, for example, files that store one or more modules, sub-programs, or portions of code. A computer program can be deployed to be executed on one computer or on multiple computers that are located at one site or distributed across multiple sites and interconnected by a communication network.

While portions of the programs illustrated in the various figures can be illustrated as individual components, such as units or modules, that implement described features and functionality using various objects, methods, or other processes, the programs can instead include a number of sub-units, sub-modules, third-party services, components, libraries, and other components, as appropriate. Conversely, the features and functionality of various components can be combined into single components, as appropriate. Thresholds used to make computational determinations can be statically, dynamically, or both statically and dynamically determined.

Described methods, processes, or logic flows represent one or more examples of functionality consistent with the present disclosure and are not intended to limit the disclosure to the described or illustrated implementations, but to be accorded the widest scope consistent with described principles and features. The described methods, processes, or logic flows can be performed by one or more programmable computers executing one or more computer programs to perform functions by operating on input data and generating output data. The methods, processes, or logic flows can also be performed by, and apparatus can also be implemented as, special purpose logic circuitry, for example, a CPU, an FPGA, or an ASIC.

Computers for the execution of a computer program can be based on general or special purpose microprocessors, both, or another type of CPU. Generally, a CPU will receive instructions and data from and write to a memory. The essential elements of a computer are a CPU, for performing or executing instructions, and one or more memory devices for storing instructions and data. Generally, a computer will also include, or be operatively coupled to, receive data from or transfer data to, or both, one or more mass storage devices for storing data, for example, magnetic, magneto-optical disks, or optical disks. However, a computer need not have such devices. Moreover, a computer can be embedded in another device, for example, a mobile telephone, a personal digital assistant (PDA), a mobile audio or video player, a game console, a global positioning system (GPS) receiver, or a portable memory storage device.

Non-transitory computer-readable media for storing computer program instructions and data can include all forms of media and memory devices, magnetic devices, magneto optical disks, and optical memory device. Memory devices include semiconductor memory devices, for example, random access memory (RAM), read-only memory (ROM), phase change memory (PRAM), static random access memory (SRAM), dynamic random access memory (DRAM), erasable programmable read-only memory (EPROM), electrically erasable programmable read-only memory (EEPROM), and flash memory devices. Magnetic devices include, for example, tape, cartridges, cassettes, internal/removable disks. Optical memory devices include, for example, digital video disc (DVD), CD-ROM, DVD+/−R, DVD-RAM, DVD-ROM, HD-DVD, and BLURAY, and other optical memory technologies. The memory can store various objects or data, including caches, classes, frameworks, applications, modules, backup data, jobs, web pages, web page templates, data structures, database tables, repositories storing dynamic information, or other appropriate information including any parameters, variables, algorithms, instructions, rules, constraints, or references. Additionally, the memory can include other appropriate data, such as logs, policies, security or access data, or reporting files. The processor and the memory can be supplemented by, or incorporated in, special purpose logic circuitry.

To provide for interaction with a user, implementations of the subject matter described in this specification can be implemented on a computer having a display device, for example, a CRT (cathode ray tube), LCD (liquid crystal display), LED (Light Emitting Diode), or plasma monitor, for displaying information to the user and a keyboard and a pointing device, for example, a mouse, trackball, or trackpad by which the user can provide input to the computer. Input can also be provided to the computer using a touchscreen, such as a tablet computer surface with pressure sensitivity, a multi-touch screen using capacitive or electric sensing, or another type of touchscreen. Other types of devices can be used to interact with the user. For example, feedback provided to the user can be any form of sensory feedback. Input from the user can be received in any form, including acoustic, speech, or tactile input. In addition, a computer can interact with the user by sending documents to and receiving documents from a client computing device that is used by the user.

The term "graphical user interface," or "GUI," can be used in the singular or the plural to describe one or more graphical user interfaces and each of the displays of a particular graphical user interface. Therefore, a GUI can represent any graphical user interface, including but not limited to, a web browser, a touch screen, or a command line interface (CLI) that processes information and efficiently presents the information results to the user. In general, a GUI can include a plurality of user interface (UI) elements, some or all associated with a web browser, such as interactive fields, pull-down lists, and buttons. These and other UI elements can be related to or represent the functions of the web browser.

Implementations of the subject matter described in this specification can be implemented in a computing system that includes a back-end component, for example, as a data server, or that includes a middleware component, for example, an application server, or that includes a front-end component, for example, a client computer having a graphical user interface or a Web browser through which a user can interact with an implementation of the subject matter described in this specification, or any combination of one or more such back-end, middleware, or front-end components. The components of the system can be interconnected by any form or medium of wireline or wireless digital data communication (or a combination of data communication), for example, a communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) using, for example, 802.11 a/b/g/n or 802.20 (or a combination of 802.11x and 802.20 or other protocols consistent with the present disclosure), all or a portion of the Internet, another communication network, or a combination of communication networks. The communication network can communicate with, for example, Internet Protocol (IP) packets, Frame Relay frames, Asynchronous Transfer Mode (ATM) cells, voice, video, data, or other information between networks addresses.

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of what can be claimed, but rather as descriptions of features that can be specific to particular implementations. Certain features that are described in this specification in the context of separate implementations can also be implemented, in combination, in a single implementation. Conversely, various features that are described in the context of a single implementation can also be implemented in multiple implementations, separately, or in any sub-combination. Moreover, although previously described features can be described as acting in certain combinations and even initially claimed as such, one or more features from a claimed combination can, in some cases, be excised from the combination, and the claimed combination can be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations can be considered optional), to achieve desirable results. In certain circumstances, multitasking or parallel processing (or a combination of multitasking and parallel processing) can be advantageous and performed as deemed appropriate.

Moreover, the separation or integration of various system modules and components in the previously described implementations should not be understood as requiring such separation or integration in all implementations, and it should be understood that the described program components and systems can generally be integrated together in a single software product or packaged into multiple software products.

Furthermore, any claimed implementation is considered to be applicable to at least a computer-implemented method; a non-transitory, computer-readable medium storing computer-readable instructions to perform the computer-implemented method; and a computer system comprising a computer memory interoperably coupled with a hardware processor configured to perform the computer-implemented method or the instructions stored on the non-transitory, computer-readable medium.

What is claimed is:

1. A computer-assisted method for managing a set of downhole sampling tools each comprising a respective inlet probe, the method comprising:
   accessing a database hosting records of the set of downhole sampling tools, wherein the records include historical data measurements and real-time data measurements corresponding to an operation of the set of downhole sampling tools when sampling reservoir formations;
   identifying, by analyzing the records of the set of downhole sampling tools, a parameter that characterizes a temporal attribute of the operation of a downhole sampling tool;
   measuring a performance metric for each of the set of downhole sampling tools based on the parameter, wherein the performance metric measures a duration between a first time point when one of the set of downhole sampling tool is activated to a second time point when the respective inlet probe on the downhole sampling tool detects a reservoir fluid from the reservoir formations;
   identifying a particular downhole sampling tool from the set of downhole sampling tools based on a comparison of measured performance metrics of the set of downhole sampling tools; and
   deploying the particular downhole sampling tool to sample a reservoir formation in a wellbore at a drilling site.

2. The computer-assisted method of claim 1, further comprising:
   selecting the particular downhole sampling tool whose respective performance metric measured using the parameter is less than the measured performance metrics corresponding to other downhole sampling tools from the set of downhole sampling tools.

3. The computer-assisted method of claim 2, wherein selecting the particular downhole sampling tool further comprises:
   filtering the records of operating the set of downhole sampling tools based on at least one of: a formation type or a formation mobility with respect to the reservoir formations being sampled.

4. The computer-assisted method of claim 1, further comprising:
   providing, to the database, records of conducting at least one upcoming downhole sampling job using the particular downhole sampling tool.

5. The computer-assisted method of claim 4, further comprising:

measuring, based on updated records of operating the set of downhole sampling tools, performance metrics of the set of downhole sampling tools.

6. The computer-assisted method of claim 5, further comprising:
in response to the measured performance metrics indicating a respective performance metric of the particular downhole sampling tool has deteriorated, selecting, from the set of downhole sampling tools, another downhole sampling tool.

7. The computer-assisted method of claim 1, wherein each respective inlet probe comprises one of: a fluid sound speed sensor, a fluid density sensor, a fluid capacitance sensor, a fluid resistivity sensor, a gas refractometer, or an optical absorption spectrometry.

8. A computer system for managing a set of downhole sampling tools each comprising a respective inlet probe, the computer system comprising one or more computer processors configured to perform operations of:
accessing a database hosting records of the set of downhole sampling tools, wherein the records include historical data measurements and real-time data measurements corresponding to an operation of the set of downhole sampling tools when sampling reservoir formations;
identifying, by analyzing the records of the set of downhole sampling tools, a parameter that characterizes a temporal attribute of the operation of a downhole sampling tool;
measuring a performance metric for each of the set of downhole sampling tools based on the parameter, wherein the performance metric measures a duration between a first time point when one of the set of downhole sampling tool is activated to a second time point when the respective inlet probe on the downhole sampling tool detects a reservoir fluid from the reservoir formations;
identifying a particular downhole sampling tool from the set of downhole sampling tools based on a comparison of measured performance metrics of the set of downhole sampling tools; and
deploying the particular downhole sampling tool to sample a reservoir formation in a wellbore at a drilling site.

9. The computer system of claim 8, wherein the operations further comprise:
selecting the particular downhole sampling tool whose respective performance metric measured using the parameter is less than the measured performance metrics corresponding to other downhole sampling tools from the set of downhole sampling tools.

10. The computer system of claim 9, wherein selecting the particular downhole sampling tool further comprises:
filtering the records of operating the set of downhole sampling tools based on at least one of: a formation type or a formation mobility with respect to the reservoir formations being sampled.

11. The computer system of claim 8, wherein the operations further comprise:
providing, to the database, records of conducting at least one upcoming downhole sampling job using the particular downhole sampling tool.

12. The computer system of claim 11, wherein the operations further comprise:
measuring, based on updated records of operating the set of downhole sampling tools, performance metrics of the set of downhole sampling tools.

13. The computer system of claim 12, wherein the operations further comprise:
in response to the measured performance metrics indicating a respective performance metric of the particular downhole sampling tool has deteriorated, selecting, from the set of downhole sampling tools, another downhole sampling tool.

14. The computer system of claim 8, wherein each respective inlet probe comprises one of: a fluid sound speed sensor, a fluid density sensor, a fluid capacitance sensor, a fluid resistivity sensor, a gas refractometer, or an optical absorption spectrometry.

15. A non-transitory computer-readable medium comprising software instructions, which, when executed by one or more computer processors, cause the one or more computer processors to perform operations of:
accessing a database hosting records of a set of downhole sampling tools, wherein the records include historical data measurements and real-time data measurements corresponding to an operation of the set of downhole sampling tools when sampling reservoir formations;
identifying, by analyzing the records of the set of downhole sampling tools, a parameter that characterizes a temporal attribute of the operation of a downhole sampling tool;
measuring a performance metric for each of the set of downhole sampling tools based on the parameter, wherein the performance metric measures a duration between a first time point when one of the set of downhole sampling tool is activated to a second time point when a respective inlet probe on the downhole sampling tool detects a reservoir fluid from the reservoir formations;
identifying a particular downhole sampling tool from the set of downhole sampling tools based on a comparison of measured performance metrics of the set of downhole sampling tools; and
deploying the particular downhole sampling tool to sample a reservoir formation in a wellbore at a drilling site.

16. The non-transitory computer-readable medium of claim 15, wherein the operations further comprise:
selecting the particular downhole sampling tool whose respective performance metric measured using the parameter is less than the measured performance metrics corresponding to other downhole sampling tools from the set of downhole sampling tools.

17. The non-transitory computer-readable medium of claim 16, wherein selecting the particular downhole sampling tool further comprises:
filtering the records of operating the set of downhole sampling tools based on at least one of: a formation type or a formation mobility with respect to the reservoir formations being sampled.

18. The non-transitory computer-readable medium of claim 15, wherein the operations further comprise:
providing, to the database, records of conducting at least one upcoming downhole sampling job using the particular downhole sampling tool.

19. The non-transitory computer-readable medium of claim 18, wherein the operations further comprise:
measuring, based on updated records of operating the set of downhole sampling tools, performance metrics of the set of downhole sampling tools; and
in response to the measured the performance metrics indicating the respective the performance metric of the particular downhole sampling tool has deteriorated, selecting, from the set of downhole sampling tools, another downhole sampling tool.

20. The non-transitory computer-readable medium of claim 15, wherein each respective inlet probe comprises one of: a fluid sound speed sensor, a fluid density sensor, a fluid capacitance sensor, a fluid resistivity sensor, a gas refractometer, or an optical absorption spectrometry.

* * * * *